(12) United States Patent
Reinshagen et al.

(10) Patent No.: US 9,186,227 B2
(45) Date of Patent: Nov. 17, 2015

(54) METHOD FOR DOPING OR COLORING CERAMICS, GLASS CERAMICS, OR GLASS

(75) Inventors: Jörg Reinshagen, Pforzheim (DE); Sascha Cramer von Clausbruch, Lienzingen (DE)

(73) Assignee: Ivoclar Vivadent AG, Schaan (LI)

( * ) Notice: Subject to any disclaimer, the term of this patent is extended or adjusted under 35 U.S.C. 154(b) by 42 days.

(21) Appl. No.: 14/115,686

(22) PCT Filed: May 11, 2012

(86) PCT No.: PCT/EP2012/058818
§ 371 (c)(1),
(2), (4) Date: Jan. 27, 2014

(87) PCT Pub. No.: WO2012/156325
PCT Pub. Date: Nov. 22, 2012

(65) Prior Publication Data
US 2014/0135200 A1    May 15, 2014

(30) Foreign Application Priority Data
May 13, 2011   (DE) .......................... 10 2011 101 661

(51) Int. Cl.
| | | |
|---|---|---|
| A61C 13/00 | (2006.01) | |
| A61C 13/08 | (2006.01) | |
| A61K 6/00 | (2006.01) | |
| A61K 6/02 | (2006.01) | |
| A61K 6/027 | (2006.01) | |
| C04B 35/111 | (2006.01) | |
| C04B 35/486 | (2006.01) | |
| C04B 35/626 | (2006.01) | |
| C04B 35/628 | (2006.01) | |
| A61C 13/20 | (2006.01) | |

(52) U.S. Cl.
CPC ............... *A61C 13/082* (2013.01); *A61C 13/20* (2013.01); *A61K 6/0094* (2013.01); *A61K 6/024* (2013.01); *A61K 6/0273* (2013.01); *A61K 6/0276* (2013.01); *C04B 35/111* (2013.01); *C04B 35/486* (2013.01); *C04B 35/6263* (2013.01); *C04B 35/6264* (2013.01); *C04B 35/62685* (2013.01); *C04B 35/62695* (2013.01); *C04B 35/62805* (2013.01); *C04B 35/62815* (2013.01); *C04B 35/62818* (2013.01); *C04B 35/62826* (2013.01); *C04B 2235/3217* (2013.01); *C04B 2235/3225* (2013.01); *C04B 2235/3272* (2013.01); *C04B 2235/443* (2013.01); *C04B 2235/5436* (2013.01); *C04B 2235/5445* (2013.01); *C04B 2235/5481* (2013.01); *C04B 2235/9661* (2013.01)

(58) Field of Classification Search
CPC ............... A61C 13/00; A61C 13/0006; A61C 13/0012; A61C 13/083; B29C 41/22; B29C 41/18
USPC ............................................... 264/17, 20, 245
See application file for complete search history.

(56) References Cited

U.S. PATENT DOCUMENTS

| | | | | |
|---|---|---|---|---|
| 4,940,523 | A * | 7/1990 | Takeshima | ............... 204/192.12 |
| 5,238,881 | A | 8/1993 | Norris | |
| 5,263,858 | A | 11/1993 | Yoshida et al. | |
| 6,709,694 | B1 * | 3/2004 | Suttor et al. | .................. 427/2.26 |
| 8,034,264 | B2 * | 10/2011 | Ritzberger et al. | ............. 264/17 |
| 8,178,012 | B1 * | 5/2012 | Khan et al. | ...................... 264/20 |
| 2007/0292597 | A1 * | 12/2007 | Ritzberger et al. | .......... 427/2.29 |
| 2009/0246735 | A1 | 10/2009 | Rogowski et al. | |
| 2009/0291316 | A1 * | 11/2009 | Rauch et al. | ................ 428/542.2 |

FOREIGN PATENT DOCUMENTS

| | | |
|---|---|---|
| DE | 19904522 A1 | 8/2000 |
| DE | 102006052030 A1 | 5/2008 |
| DE | 102008026980 A1 | 12/2009 |
| EP | 1486476 A1 | 12/2004 |
| EP | 2123185 A2 | 11/2009 |

* cited by examiner

*Primary Examiner* — Noah Wiese
(74) *Attorney, Agent, or Firm* — Ann M. Knab; Thad McMurray

(57) ABSTRACT

In a method of doping or of coloring ceramic, glass ceramic or glass, the ceramic, the glass ceramic or the glass is provided as granular material and this granular material is brought into contact with a solution which contains metal ions and/or metal complexes. This method is used in particular in the production of shaped bodies that consist at least partly of the mentioned materials. In this way, preferably a shaped body of dental ceramic is produced.

23 Claims, No Drawings

METHOD FOR DOPING OR COLORING CERAMICS, GLASS CERAMICS, OR GLASS

CROSS-REFERENCE TO RELATED APPLICATIONS

This application is a National Stage application of International patent application PCT/EP2012/058818, filed on May 11, 2012, which claims priority to German patent application No. 102011101661 filed on May 13, 2011, the disclosures of which are incorporated herein by reference in their entirety.

The invention relates to a method of doping or of colouring ceramic, glass ceramic or glass as well as the materials produced therewith. The invention furthermore relates to shaped bodies, in particular dental shaped bodies that are produced from the corresponding materials, as well as dental prostheses that are in turn produced from such shaped bodies.

The fields of use of ceramics, in particular so-called technical ceramics, have become ever more numerous in recent years and decades due to their physical and chemical properties. Technical ceramics are ceramic materials that have been optimized, in terms of their properties, for technical applications. Here, for example, the use of such ceramics in dentistry, in particular in the production of dental prostheses, or also in the field of jewellery, can be emphasized.

In dentistry, such ceramic materials are used not only as previously for fillings and veneers, but in recent times increasingly also for producing all-ceramic prosthetic parts as dental prostheses. The dental prosthesis is often produced by machining, for example milled, using CAD/CAM technology from a shaped part, the so-called blank or ingot, which usually consists of unsintered or partly sintered ceramic. The obtained dental prosthetic parts are then finally-sintered and, optionally after a further processing by the dental technician, placed in the mouth of the patient.

If dentistry is again taken as an example for corresponding applications of technical ceramics, the ceramic materials used must thus be optimized, particularly also with respect to the new possible uses as all-ceramic, for one thing with respect to the required physical or mechanical properties and for another with respect to the desired aesthetics. Understandably, it is also desired in the case of all-ceramic dental prosthetic parts, such as for example in the case of dental frameworks, that the dental prosthesis looks as natural as possible. In this connection, for example a good colour match between the ceramic dental prosthesis and the remaining natural teeth of the patient is to be achieved. As the natural tooth colour varies considerably among different patients, it is accordingly necessary to provide a homogeneous colouring of the dental prosthesis in different colour shades.

In order to colour ceramic shaped bodies, in particular for dental applications, it is already known to admix the colouring substances dry in powder form with the corresponding ceramic material. This method is described in WO 2008/023053 A2. Metal oxides, such as iron oxide, which are likewise admixed in powder form with the powdered ceramic starting material, are used as colouring substances.

Due to the fact that the colouring substances are used in powder form per se, the method according to WO 2008/023053 A2 appears in particular suitable for the production of large quantities of coloured ceramic materials. The production of smaller quantities of coloured ceramic, in particular a larger number of smaller batches with individual colour shades, is not discussed in this document.

However, the procedures in which a porous shaped body made of ceramic is coloured with the help of solutions which contain metal ions or metal complexes are still well-established in practice. These shaped bodies can be the mentioned blanks or ingots, or in particular also the dental prosthetic parts shaped/milled from these blanks.

As a rule, the porous shaped body made of ceramic is dipped into the dye solution, or the dye solution is applied to the ceramic with a suitable applicator. In this way, the dye solution partly or fully penetrates the porous ceramic part. The thus-treated ceramic is then dried and sintered, whereby the final colouring forms.

Corresponding colouring methods are described in WO 00/46168 A1, EP 1 486 476 A1 or also in WO 2009/146804 A1.

However, the described methods that use dye solutions have the disadvantage that every individual blank/ingot or every prosthetic part machined from such blanks must be coloured individually. Not only is this associated with a considerable outlay for the user, usually the dental technician. In addition, variations in the final colour of different parts cannot always be avoided, despite careful observance of all method parameters.

The object of the invention is accordingly to avoid the outlined and further disadvantages of the described state of the art. In particular, a method of colouring ceramic, glass ceramic or glass is to be provided which makes possible a relatively easy colouring with reproducible results not only for relatively large, but also for smaller quantities of material. In this way, it shall be achieved that the user, for example the dental technician, can be provided with shaped bodies, such as for example blanks, with different colour shades, without difficulty.

The method shall be designed such that it is in principle not limited to the colouring of the mentioned materials, but that these materials can also be doped in a targeted manner with additional elements which thus do not necessarily have a colouring effect but which effect a change in the material properties for the desired intended use.

This object is achieved by the method with the features of claim 1. Preferred embodiments of this method are described in the dependent claims 2 to 11. Claim 12 defines the ceramic, the glass ceramic or the glass which are obtainable or are obtained with the claimed method. Claims 13 and 14 define the shaped bodies which are produced from the materials according to the invention. The dental prosthesis itself, which results from the claimed shaped bodies, is defined in claim 15.

The wording of all of the claims is hereby incorporated into the content of this description by reference.

The method according to the invention of the type mentioned at the outset is provided in particular for the production of shaped bodies that at least partly consist of ceramic, glass ceramic or glass. In this method, the ceramic, the glass ceramic or the glass is provided as granular material and this granular material is then brought into contact with a solution which contains metal ions and/or metal complexes.

In this connection, the terms used in connection with claim 1 are to be explained as follows:

By "doping" is meant the preferably targeted incorporation of metals or metal ions into the materials used according to the invention (ceramic, glass ceramic, glass). This incorporation is usually carried out such that the metal atoms or metal ions occupy spaces that were previously occupied by other atoms, or such that they are positioned between such spaces. In the case of crystalline or partly crystalline materials, these spaces can accordingly be lattice sites or also interstitial lattice sites. Alternatively, the metal atoms/metal ions can also accumulate on grain boundaries or form deposits, in particular nanoparticulate or colloidal deposits, inside the material, for example in the case of glass.

If the incorporated metal atom or metal ion has a colouring effect or if it shows such a colouring effect in the material, reference is thus to be made according to the invention to a "colouring".

By "ceramic" is meant according to the invention inorganic, non-metallic materials which are largely crystalline, i.e. made of crystallites/grains. As a rule, a "glass ceramic" has crystalline (ceramic) areas in an amorphous (glass) matrix. "Glass" is an amorphous, non-crystalline solid. It is an amorphous substance which can be described thermodynamically as frozen, supercooled liquid.

"Granular material" is intended to mean a material in which several or many grains/crystallites have coalesced into larger particles, as a rule with the help of binders, in particular organic binders. These (larger) particles are preferably uniform, e.g. ellipsoidal or in particular spherical. Located between these particles are pores which can also have the shape of narrower, elongated capillaries. Such pores can also be located inside the particles themselves.

As a rule, granular materials are free-flowing, in particular in the dry state, and can be produced by different processes known to a person skilled in the art, for example by spray-granulation.

The term "solution" used is immediately familiar to a person skilled in the art and is to be understood here as broadly as possible. A (liquid) solution is the homogeneous mixture of a corresponding solid in at least one solvent.

As stated above, a decisive feature of the method according to the invention is that the ceramic, the glass ceramic or the glass is brought into contact as a granular material, i.e. as a material already coalesced into larger particles, with a solution containing metal ions or metal complexes.

This contacting can be carried out in different ways. Thus it is possible to mix the solution with the granular material. Depending on the selection, concentrated or diluted solutions can be used. As a rule, in the case of more diluted solutions larger quantities of liquid are available. Therefore, it is even conceivable to cover the granular material completely with the solution and thus to effectively soak it with the solution. After removal of the solvent, the metal ions then remain on the granular material or in the granular material.

It is important that the metal ions or metal complexes that are contained in the solution are distributed as evenly as possible on the granular material or in the granular material. In this way, it is then ensured that the doping and/or colouring metal ions are also distributed as evenly as possible in the resulting shaped body.

In this connection, it is advantageous if in the invention the granular material is sprayed with the solution or the solution is sprayed into the granular material. For one thing, the metal ions are thus distributed as evenly as possible on or in the granular material. For another thing, with such a spray procedure, the solution is only applied/incorporated in the quantity which is actually necessary for the doping/colouring. The solution is thus used sparingly.

Often the obtained treated granular material can be further processed directly, in particular as a free-flowing or flowable product, optionally with a (residual) moisture. As a rule, this residual moisture is less than 20%, in particular between 5 and 15%.

In a further embodiment, it can also be advantageous if the granular material treated with the solution (after the contacting or spraying) is dried. In this way, the solvent or solvent mixture used for producing the solution is largely removed before the further processing of the treated granular material. This can be important in particular if such a further processing is to take place dry, for example by dry pressing.

Moreover, it is also possible to dry the granular material in a separate step before the treatment with the solution.

For the described drying, as a rule temperatures below 150° C., in particular below 100° C., will be sufficient. Such temperatures are suitable to remove customary solvents, for example the alcohols described below, from the granular material.

In the case of further preferred embodiments of the method according to the invention, the granular material is moved during the contacting, preferably during spraying with the solution. This movement can be for example a circulation or stirring of the granular material. This can be achieved for example by means of air or a gas, such as nitrogen or argon, or by means of a suitable stirring device.

Alternatively, the movement, in particular circulation or stirring, can also first take place during the additional drying step. It is also possible and advantageous to apply this movement both during the contacting and during drying.

The movement during the contacting improves the distribution of the metal ions from the solution on or in the granular material. The movement during drying supports the removal of the solvent during the drying process.

It is further preferred in the method according to the invention if the solution contains metal ions or metal complexes of the rare earth elements or of the sub-group elements of the periodic table of the elements. As is known, the group of lanthanoids is in particular also comprised by the rare earth elements.

In the case of the sub-group elements, in particular the transition metals from the sub-groups III B, IV B, V B, VI B, VII B, VIII B, I B, II B are to be emphasized. Taking the newer nomenclature of the periodic table of the elements as a basis, these are thus groups 3, 4, 5, 6, 7, 8, 11 and 12.

In the method according to the invention it is particularly preferred to use solutions which contain metal ions or metal complexes with at least one of the elements iron (Fe), chromium (Cr), copper (Cu), yttrium (Y), praseodymium (Pr), cobalt (Co), nickel (Ni), manganese (Mn), erbium (Er) or cerium (Ce).

In the method according to the invention, the solution which is provided for doping or colouring advantageously contains metal ions or metal complexes of alkaline earth metals, in particular of calcium and/or magnesium. Alternatively or in addition, aluminium ions or aluminium complexes can also be contained. In this way, the materials (ceramic, glass ceramic, glass) can also be doped with alkaline earth metals or with aluminium.

As a rule, the mentioned solutions can be produced according to the invention in that a corresponding metal salt is taken up, in particular dissolved, in the corresponding solvent or solvent mixture. In the invention, the corresponding salts, such as halides, in particular chlorides, sulphates, carbonates or in particular nitrates of the respective metal, are preferably used as starting materials.

The solution can optionally contain (additional) complexing agents which then form the corresponding complex compounds with the metals or metal ions. The complexing agents involved can be the inorganic complexing agents known to a person skilled in the art or the known organic complexing agents, such as acetylacetone, EDTA (ethylenediaminetetraacetate) or NTA (nitrilotriacetic acid).

In principle, a very wide variety of solvents can be used as solvents for producing the solutions used, in particular polar solvents. These can be inter alia polar organic solvents, such as aliphatic alcohols, in particular methanol, ethanol, among others. In particular, however, water on its own or water mixed with organic polar solvents, preferably alcohols, can also be used as solvent. The solution can optionally also contain so-called stabilizers, dispersants and similar, in addition to the mentioned complexing agents.

In the invention, the concentration of the metal ions or metal complexes in the solution can be varied within broad limits. What is decisive is that the metal ion/metal complex is brought into contact with the granular material in solution, i.e. together with the corresponding solvent. In this way, as explained, an even distribution of the metal ions provided for doping or colouring on or in the granular material is ensured.

The metal ions or metal complexes are preferably contained in the solution in a concentration between 0.01 wt.-% and 70 wt.-%, preferably between 0.1 wt.-% and 50 wt.-%. Within the last-mentioned range, in particular concentrations between 2 wt.-% and 25 wt.-% are preferred.

Depending on the colouring effect of the individual metal ions, either smaller quantities of metal ions are sufficient or larger quantities of metal ions are required. It is understood that, depending on the colour shade to be achieved, also at least two different metal ions can be included in the solution. This is achieved in that at least two metal salts, optionally with the addition of complexing agents, are dissolved in the corresponding solvent or solvent mixture.

It is also possible according to the invention to relate the total quantity of solution used for doping or colouring to the quantity of powder that is treated with the solution. Here too a variation of the quantity ratios within broad limits is possible. Quantities of between 0.0001-1 g solution per g quantity of granular material, in particular 0.001-0.5 g solution per g quantity of granular material, are preferred.

The amount of the solution in the treated material is preferably ≤20 wt.-%, in particular ≤15 wt.-%. Below the named upper limits, in particular with amounts of between 5 and 15 wt.-%, treated granular materials that are not too moist are obtained, which, as free-flowing products, can be further processed directly into blanks by dry-pressing.

As outlined above, the material to be doped or the material to be coloured is used as granular material. The average particle size of this granular material (D50) is preferably between 1 μm and 200 μm, in particular between 5 μm and 100 μm. The granular material can in turn be formed from powders with an average particle size (D50) of between 1 nm and 50 μm, preferably between 10 nm and 10 μm. Within the last-mentioned range, average particle sizes between 100 nm (0.1 μm) and 1 μm are preferred.

According to the invention, the granular material, after it has been contacted with the solution and optionally after the subsequent drying, is preferably further processed directly to form a shaped body. The shaped body can be prepared in a wide variety of ways. In particular, a pressing procedure, in particular a dry pressing procedure, is involved.

With such pressing procedures or pressing steps, the ceramic, glass-ceramic or glass material, i.e. the material treated according to the invention, is pressed into a mould using a high pressure. This pressing can take place either from only one direction axially (uniaxially) or from both directions axially (biaxially). An isostatic pressing is also possible. Here, the distinction is drawn between a full isostatic pressing in which an exposure to pressure takes place simultaneously from all directions with equal pressing pressure and a quasi-isostatic pressing in which pressing is carried out biaxially and radially simultaneously with a cylindrical mould. Depending on material and pressing pressures, the desired microstructures and strengths can be achieved with all types of pressing.

For the final completion of the shaped body, as a rule the organic binder or pressing auxiliary present can be removed (debound) after the pressing procedure. This is followed, in particular in the case of ceramic materials, by a sintering at a higher temperature in order to further reduce the porosity of the material. However, as a rule final-sintering is not carried out here in order to ensure subsequently an easier mechanical processability of the material.

If in the present case a ceramic is doped or coloured, this is preferably a ceramic based on zirconium oxide or aluminium oxide. To be particularly emphasized here are the so-called technical ceramics mentioned at the outset which are immediately familiar to a person skilled in the art.

If dental ceramics are treated, these are preferably ceramics which comprise constituents such as zirconium oxide, yttrium oxide, hafnium oxide, aluminium oxide and optionally further oxides.

If glasses are treated according to the invention, these are preferably silicate glasses or oxidic glasses and in particular borosilicate glasses or aluminosilicate glasses. Alkali borosilicate glasses are particularly preferred, as they can be prepared particularly well as amorphous, porous solid bodies. By definition, such alkali borosilicate glasses comprise, as constituents, alkali metal oxides, as a rule sodium oxide ($Na_2O$) and/or potassium oxide ($K_2O$) and boron trioxide ($B_2O_3$). Further constituents, as a rule main constituents, are silicon dioxide ($SiO_2$) and aluminium oxide ($Al_2O_3$).

In summary, the core of the present invention is that a doping, in particular colouring, of the corresponding material, in particular a dental ceramic, is carried out on a granulated material by means of a solution which comprises metal ions and/or metal complexes. Accordingly, no powdered materials are mixed with one another and also no powdered material with a solution, but instead a granulated starting material is brought into contact with the (colouring) solution according to the invention. This starting material is absorbent due to the pores and capillaries present in it and accordingly readily wettable by the solution, with the result that the solution can penetrate well the pores/capillaries present and fill them, in particular essentially completely fill them.

Accordingly, the invention is integrated as follows for example into the process chain for producing a dental shaped part.

Firstly, a granular material of the corresponding material, for example the dental ceramic, is produced or provided. This granular material is contacted, in particular sprayed (and mixed), with the (colouring) solution. In this way, a (coloured) granular material is obtained which as a rule is still moist and, as free-flowing material, can be pressed directly into a corresponding blank.

It is to be emphasized that according to the invention a granular material treated with the solution is provided, wherein the (colouring) solution is stored essentially in the pores or in the capillaries, i.e. inside the particles of the granular material. Accordingly the treated granular material, viewed macroscopically, is substantially dry from the outside and in this way retains the essential properties of a (dry) granular material, i.e. its flowability and its ability to be pressed dry into a shaped body.

A drying of the treated granular material before the pressing is merely optional. Optionally, the treated (coloured) granular material can be mixed before the pressing either with uncoloured granular material or with granular materials coloured in some other way, in order to obtain either lighter colour shades or mixed colour shades. For the pressing procedure, as a rule the treated granular material additionally contains a customarily used (known), for example organic, binder. After the pressing, this binder is removed from the obtained blank by a heat treatment (debinding), and as a rule the blank is sintered, but not finally-sintered. In this way, the blank can easily be machined, for example by milling, in order to obtain from it dental prosthesis parts, such as frameworks for crowns and bridges, veneers or also finished ceramic parts such as crowns and bridges. The thus-obtained dental prosthesis is densely- or finally-sintered in a furnace, with the result that a coloured dental prosthesis can be obtained in this way which is finished and placed in the mouth of the patient in customary manner by the dental technician and by the dentist.

In addition, the invention comprises the ceramic, the glass ceramic or the glass which is producable or is produced with the described method according to the invention. In particular the mentioned material is a ceramic, for dental applications preferably a feldspar ceramic or lithium disilicate ceramic.

Also comprised by the invention is a shaped body, in particular a dental shaped body, which is produced from the material (ceramic, glass ceramic, glass) according to the invention. This shaped body is in particular an unsintered or not finally-sintered blank for the producing of dental prostheses, preferably all-ceramic dental prostheses. This shaped body, for example due to its porosity, preferably easily machinable, in particular by milling, with the result that in this way the dental prosthesis can be manufactured for example in the form of frameworks, crowns, bridges and the like.

The mentioned shaped body is preferably a so-called blank or ingot with in principle any geometry. Such blanks can be cuboidal, cubic or cylindrical. Any other geometries, such as for example conical or spherical blanks, are also possible. In particular cylindrical blanks can preferably be discoidal blanks. By definition a disk is a body, in particular a cylinder, the thickness of which is substantially smaller than its radius. The disk is preferably round, but can also have other geometries, for example a shape that corresponds substantially to the outline of a horseshoe.

Finally, the invention also comprises the dental prosthesis, for example the framework, the crown or the bridge or also the veneer, which is produced from the claimed shaped body according to the invention.

The invention is associated with a whole range of advantages.

Because of the design of the method according to the invention, disadvantages of the known methods described at the outset can be avoided. Because of the fact that not every individual blank or every individual manufactured dental prosthesis part need to be coloured, possible process errors can be avoided. The dental technician is provided with a reproducibly coloured blank from which he can manufacture several dental prosthesis parts with constant colouring.

On the other hand, it is not necessary to add the colouring metal ions as powder, for example as metal oxides, to a ceramic powder. Because the metal ions are contacted with the starting material, which is present as granular material, via a solution, smaller quantities of starting material can also be reliably and reproducibly doped or coloured with the metal ions. Thus, if required, small series of blanks with a specific colouring can also be produced. On the one hand, this allows the doping or colouring close to the starting material, while on the other hand the disadvantages of the colouring on the finished product as it is currently predominantly used can be avoided.

A further advantage is that a shaping of the material treated according to the invention, for example to form the mentioned blanks, can directly follow the doping/colouring. Further intermediate steps such as a calcining (heating), granulation or another treatment are not necessary.

The mentioned features and further features of the invention follow from the subsequent example in conjunction with the dependent claims. The individual features can be realized on their own or in combination with one another.

EXAMPLE

A commercially available granular material is used to start with, which can be produced as follows.

Firstly, a powder for producing a dental ceramic is provided with the following composition:

| Constituent | Formula | wt.-% |
| --- | --- | --- |
| yttrium oxide | $Y_2O_3$ | 5.36 |
| aluminium oxide | $Al_2O_3$ | 0.05 |
| zirconium oxide + yttrium oxide + hafnium oxide | $ZrO_2$ + $Y_2O_3$ + $HfO_2$ | >99.0 |
| other oxides | | remainder |

Such a composition is also known under the name 3Y-TZP (with 3 mol.-% yttria partly stabilized tetragonal zirconium oxide).

1 kg of the above-mentioned powder mixture is spray-granulated together with a proportion of 3.8 wt.-% of an organic binder, which later also serves as pressing aid. Before the spray-granulation, the average particle size (D50) of the powder is 0.43 μm. After the granulation, the average particle size of the granular material is 52 μm (D10=35 μm, D50=52 μm, D90=90 μm).

In parallel, a dye solution of 30 g iron(III) nitrate nonahydrate in 80 g demineralized water is prepared. The iron salt dissolves completely in the water.

The above-mentioned granular material (1 kg) is introduced into a laboratory-scale apparatus, which, in addition to a container with stirring device, has a spray nozzle for applying the solution of the metal salt onto the granular material. The granular material placed in the container is set in a uniform motion by means of the stirring device. As is known, the granular material, as bulk product, is flowable. The solution of the metal salt is then distributed as spray mist over the ceramic granular material with the help of the spray nozzle and thus brought into contact with the granular material. It is also possible to introduce, in particular to spray, the solution finely dispersed, i.e. nebulized, directly into the moved and/or swirled granular material, as a rule under pressure.

Because the granular material is moved by means of the stirring device, i.e. circulated, over time the whole surface of the particles of granular material comes into contact with the solution. It can also be said that the surface of the particles of the granular material is essentially uniformly wetted with the solution. In this way, the solution can in particular also penetrate pores present in the particles of the granular material and between the particles of the granular material.

In the example, all of the solution given above, which consists of 80 g demineralized water and 30 g iron(III) nitrate nonahydrate, is applied to 1 kg granular material. The applied amount of solution is thus about 10 wt.-%, relative to the total quantity of granular material.

Without prior drying, the coloured moist granular material was then pressed in a uniaxial (dry) pressing procedure with a pressing force of 1200 kN into a discoidal green body (blank) 100 mm in diameter and 16 mm thick. The thus-obtained blanks were pre-sintered at 1000° C. and then served to produce dental prostheses. Thus, for example crowns which have a good strength and a homogeneous colour distribution were milled from pre-sintered blanks.

The procedure according to the example was varied in different ways. Thus other metal salts were used to produce dye solutions, namely in different concentrations. Moreover, the coloured granular materials obtained according to the example were mixed with non-coloured granular material in order to obtain lighter colour shades. This mixing procedure was carried out for example by means of a drum hoop mixer, as is customarily used for mixing granular products.

The invention claimed is:

1. A method of doping or of coloring ceramic, glass ceramic or glass, in the production of shaped bodies which comprises the ceramic, glass ceramic or glass materials, wherein the ceramic, the glass ceramic or the glass is provided as granular material and wherein the granular material is contacted with a solution which comprises metal ions and/or metal complexes and the solution penetrates pores and/or capillaries present in the granular material.

2. The method according to claim 1, wherein the granular material is sprayed with the solution.

3. The method according to claim 1, wherein the granular material treated with the solution is dried at a temperature <100° C.

4. The method according to claim 1 wherein the granular material is moved during the contacting and/or during drying.

5. The method according to claim 1, wherein the solution comprises metal ions or metal complexes of one or more rare earth elements.

6. The method according to claim 5, wherein the solution comprises metal ions or metal complexes of at least one of iron, chromium, copper, yttrium, praseodymium, cobalt, nickel, manganese, erbium or cerium.

7. The method according to claim 1, wherein the solution comprises at least one polar solvent, wherein the polar solvent is preferably water or at least one aliphatic alcohol.

8. The method according to claim 1, wherein the metal ions or metal complexes are present in the solution in a concentration of between 0.01 wt.-% and 70 wt.

9. The method according to claim 1, wherein the granular material is further processed to form a shaped body.

10. The method according to claim 1, wherein the material is a ceramic based on zirconium oxide or aluminium oxide.

11. The method according to claim 10, wherein the ceramic is a dental ceramic.

12. A ceramic, glass ceramic or glass, producable or produced by the method according to claim 1.

13. A dental shaped body, produced from the ceramic, the glass ceramic or the glass according to claim 12.

14. The dental shaped body according to claim 13, comprising an unsintered or not finally-sintered blank for producing an all-ceramic dental prostheses.

15. A dental prosthesis produced from the shaped body according to claim 13.

16. The method according to claim 4, wherein the granular material is moved by circulating or stirring during the contacting.

17. The method according to claim 4, wherein contacting comprises spraying.

18. The method according to claim 5, wherein the rare earth elements comprise the lanthanoids, or the sub-group elements of the periodic table of the elements.

19. The method according to claim 7, wherein the at least one polar solvent comprises water or at least one aliphatic alcohol.

20. The method according to claim 8, wherein the metal ions or metal complexes are present in the solution in a concentration of between 0.1 wt.-% and 50 wt.-%.

21. The method according to claim 9, wherein the granular material is further processed by at least one pressing step after the contacting, and optionally after drying.

22. The method according to claim 21, wherein the at least one pressing step comprises dry pressing.

23. The method according to claim 11, wherein the dental ceramic comprises zirconium oxide, yttrium oxide, hafnium oxide and/or aluminium oxide and optionally further oxides.

* * * * *